United States Patent
Le Flohic et al.

(10) Patent No.: US 10,245,270 B2
(45) Date of Patent: Apr. 2, 2019

(54) SALT OF 3-[(3-{[4-(4-MORPHOLINYLMETHYL)-1H-PYRROL-2-YL]METHYLENE}-2-OXO-2,3-DIHYDRO-1H-INDOL-5-YL)METHYL]-1,3-THIAZOLIDINE-2,4-DIONE, ITS PREPARATION, AND FORMULATIONS CONTAINING IT

(71) Applicant: LES LABORATOIRES SERVIER, Suresnes (FR)

(72) Inventors: Alexandre Le Flohic, Fauville en Caux (FR); Jérôme Guidotti, Criquetot sur Ouville (FR); Philippe Letellier, Orléans (FR)

(73) Assignee: LES LABORATOIRES SERVIER, Suresnes (FR)

( * ) Notice: Subject to any disclaimer, the term of this patent is extended or adjusted under 35 U.S.C. 154(b) by 0 days.

(21) Appl. No.: 16/120,797

(22) Filed: Sep. 4, 2018

(65) Prior Publication Data

US 2018/0369252 A1    Dec. 27, 2018

Related U.S. Application Data

(63) Continuation-in-part of application No. 15/896,273, filed on Feb. 14, 2018, now abandoned, which is a continuation of application No. 14/904,260, filed as application No. PCT/FR2014/051783 on Jul. 11, 2014, now Pat. No. 9,925,195.

(30) Foreign Application Priority Data

Jul. 12, 2013 (FR) .................................. 13 56870

(51) Int. Cl.
  *C07D 417/14* (2006.01)
  *A61K 31/5377* (2006.01)
  *A61K 45/06* (2006.01)

(52) U.S. Cl.
  CPC .......... *A61K 31/5377* (2013.01); *A61K 45/06* (2013.01); *C07D 417/14* (2013.01)

(58) Field of Classification Search
  CPC .................................................... C07D 417/14
  See application file for complete search history.

(56) References Cited

U.S. PATENT DOCUMENTS

| | | | | |
|---|---|---|---|---|
| 8,133,889 B2* | 3/2012 | Ortuno | ................ | C07D 401/12 |
| | | | | 514/235.2 |
| 8,541,412 B2* | 9/2013 | Ortuno | ................ | C07D 401/12 |
| | | | | 514/235.2 |
| 8,653,073 B2* | 2/2014 | Ortuno | ................ | C07D 401/12 |
| | | | | 514/235.2 |
| 9,925,195 B2* | 3/2018 | Le Flohic | ............ | C07D 417/14 |
| 2011/0034460 A1* | 2/2011 | Ortuno | ................ | C07D 401/12 |
| | | | | 514/235.2 |

* cited by examiner

*Primary Examiner* — Matthew P Coughlin
(74) *Attorney, Agent, or Firm* — Hueschen and Sage

(57) ABSTRACT

3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione methanesulphonate of formula (II):

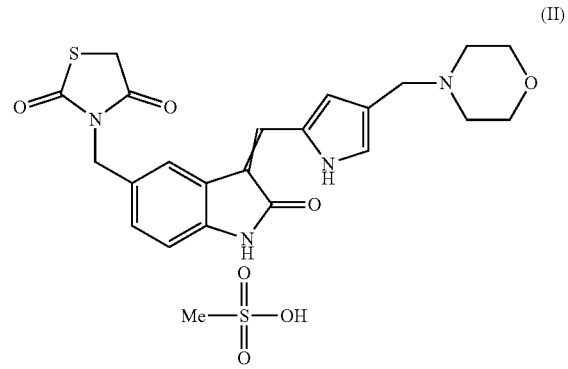

Medicinal products containing the same which are useful in treating cancer.

8 Claims, 3 Drawing Sheets

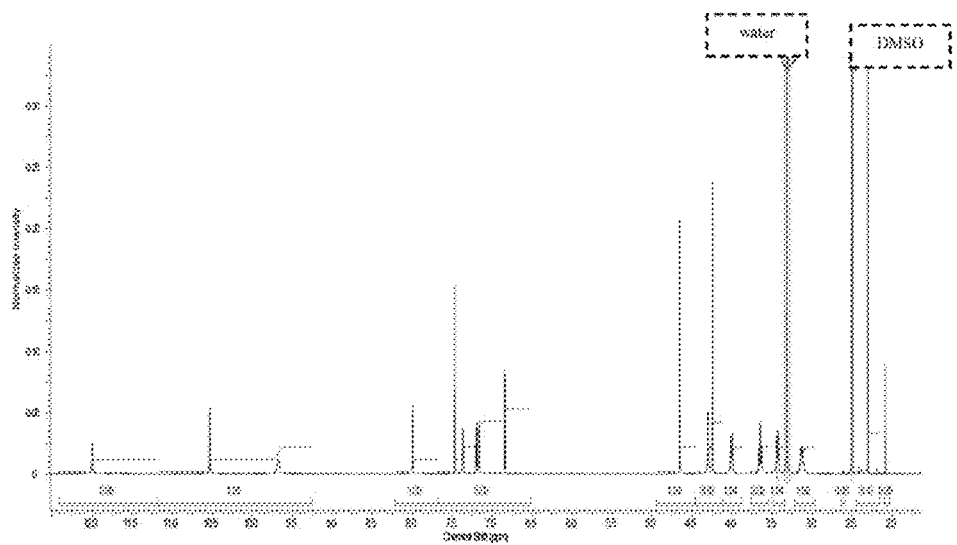
Figure 3 – ¹H NMR spectrum of the compound of Example 6

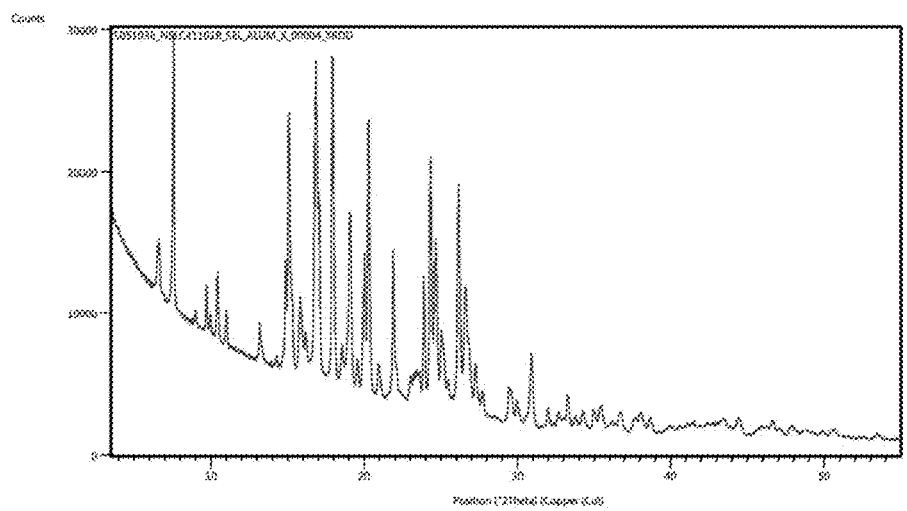
Figure 4 – XRPD diagram for the compound of Example 6
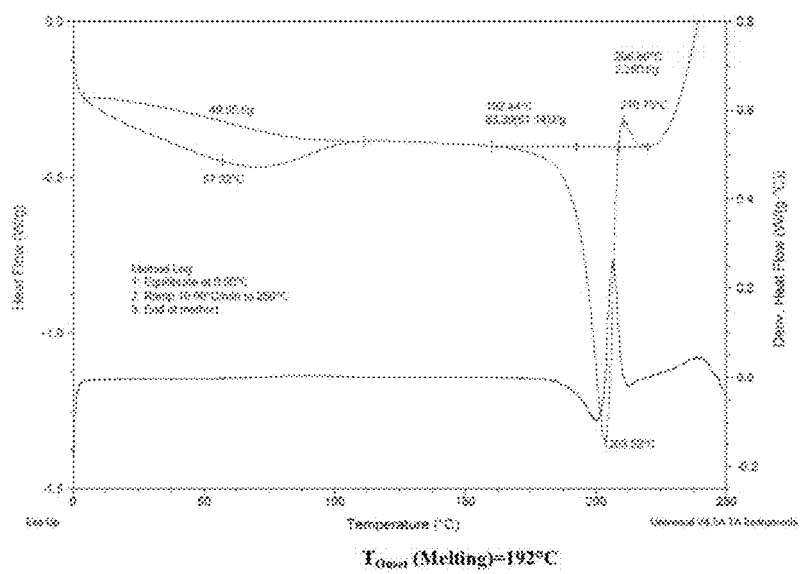
Figure 5 – DSC diagram for the compound of Example 6

SALT OF 3-[(3-{[4-(4-MORPHOLINYLMETHYL)-1H-PYRROL-2-YL]METHYLENE}-2-OXO-2,3-DIHYDRO-1H-INDOL-5-YL)METHYL]-1,3-THIAZOLIDINE-2,4-DIONE, ITS PREPARATION, AND FORMULATIONS CONTAINING IT

The present invention relates to a new salt of 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione of formula (I):

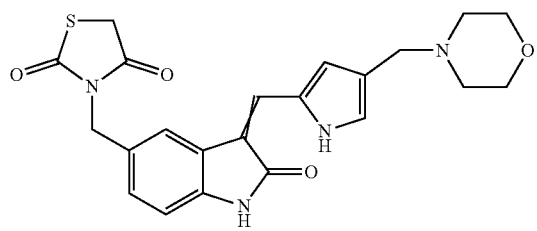

(I)

to its preparation process and also to pharmaceutical compositions containing it.

3-[(3-{[4-(4-Morpholinylmethyl)-1H-pyrrol-2-yl]methylene}-2-oxo-2,3-dihydro-1H-indol-5-yl)methyl]-1,3-thiazolidine-2,4-dione has very valuable pharmacological properties in the field of cancerology. It has in fact been shown that 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione has the ability to inhibit the migration of cancer cells, making it especially useful in the treatment of cancers and, more especially, solid metastatic tumours. Among the cancers envisaged for treatment there may be mentioned, without implying any limitation, cancers of the colon, breast, liver, kidneys, brain and esophagus, melanomas, myelomas, ovarian cancers, non-small-cell lung cancers, small-cell lung cancers, prostate and pancreatic cancers, and sarcomas.

The preparation and therapeutic use of 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione and its addition salts with a pharmaceutically acceptable acid, and more especially its hydrochloride, have been described, for example, in the European patent specification EP 2281822.

In view of the pharmaceutical value of this compound it is important to be able to obtain the active compound in excellent yields, with high purity and with excellent reproducibility. It was rapidly found that the hydrochloride which was used presented problems of purification and recrystallisation, and also a yield that was very difficult to optimise. Furthermore, problems of reproducibility and consistency of the active compound obtained were observed. After numerous research studies, it was possible to identify a new salt combining various advantages, especially relating to purification, to reproducibility of the process for obtaining it and to yield, but also unexpectedly having the advantage of very significantly improving the solubility of the active compound. This new salt accordingly has all the qualities indispensable to its use as a medicament, from both the physicochemical and the pharmacokinetic point of view.

The present invention accordingly relates to a new salt of 3-[(3-{[4-(4-morpholinylmethyl)-1H-pyrrol-2-yl]methylene}-2-oxo-2,3-dihydro-H-indol-5-yl)methyl]-1,3-thiazolidine-2,4-dione, more especially 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione methanesulphonate of formula (II):

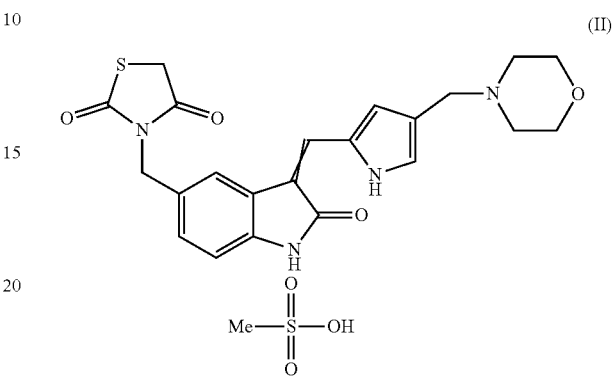

(II)

wherein the notation

means that the double bond is of configuration Z or E.

The invention preferably relates to the Z isomer of 3-[(3-{([4-(4-morpholinylmethyl)-1H-pyrrol-2-yl]methylene}-2-oxo-2,3-dihydro-1H-indol-5-yl)methyl]-1,3-thiazolidine-2,4-dione methanesulphonate.

This new salt has the following advantages:
- a simple and reproducible process for obtaining it in an excellent yield;
- increased solubility in both water and organic solvents, making it possible to envisage purification stages such as clarifications, in order to increase its purity.

The invention relates also to a process for obtaining 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione methanesulphonate, more especially its Z isomer, characterised in that there is used as starting material 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione obtained for example in accordance with a process described in the patent specification EP 2281822. The dione is dissolved in a binary system of solvent/water, then from 1 to 2 molar equivalents of methanesulphonic acid are added and the mixture is stirred until the methanesulphonate precipitates out.

The solvent will advantageously be a polar solvent such as, for example, acetonitrile, acetone, 1,4-dioxane, tetrahydrofuran, N,N-dimethylformamide, N,N-dimethylacetamide, dimethyl sulphoxide, alcohols such as methanol, ethanol and isopropanol, water and also aqueous/organic mixtures of those solvents. Preferably, the solvent/water ratio will be 0/100 to 100/0.

A variant of the process according to the invention consists of using as starting material 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione hydrochloride; the manner in which this compound is obtained has been described, for example, in the patent specification EP 2281822. The hydrochloride is dissolved in a binary system of solvent/water, and the pH of the mixture is brought to 8 by adding a base. The salt formed is removed by filtration. The filtrate is heated and then methanesulphonic acid is added. The temperature is then slowly returned to ambient temperature, and the methanesulphonate obtained is filtered off. More especially, the solvent used is a polar solvent such as acetonitrile, acetone, 1,4-dioxane, tetrahydrofuran, N,N-dimethylformamide, N,N-dimethylacetamide, dimethyl sulphoxide, or alcohols such as methanol, ethanol and isopropanol. Preferably the solvent/water ratio will be 70/30 and, more especially, 90/10. The methanesulphonic acid is used in excess, more especially from 1 to 2 equivalents.

The compound of formula (II) according to the invention has excellent stability over time even under denaturing conditions: at 25° C./60% relative humidity, at 25° C./90% relative humidity, at 30° C./65% relative humidity, at 40° C./75% relative humidity, or at 50° C., the compound of formula (II) is unchanged after 6 months.

The invention relates also to pharmaceutical compositions comprising as active ingredient the compound of formula (II) according to the invention, more especially its Z isomer, together with one or more inert, non-toxic, appropriate excipients. Among the pharmaceutical compositions according to the invention there may be mentioned more especially those that are suitable for oral, parenteral (intravenous or subcutaneous) or nasal administration, tablets or dragées, granules, sublingual tablets, capsules, lozenges, suppositories, creams, ointments, dermal gels, injectable preparations, drinkable suspensions and chewing gums.

The pharmaceutical forms comprising the compound of formula (II) according to the invention, more especially its Z isomer, will be used in the treatment of cancers and, more especially, solid metastatic tumours. Among the cancers envisaged for treatment there may be mentioned, without implying any limitation, cancers of the colon, breast, liver, kidneys, brain and esophagus, melanomas, myelomas, ovarian cancers, non-small-cell lung cancers, small-cell lung cancers, prostate and pancreatic cancers, and sarcomas.

The useful dosage can be varied according to the nature and severity of the disorder, the administration route and the age and weight of the patient. The dosage varies from 1 mg to 1 g per day, in terms of the base equivalent, in one or more administrations.

BRIEF DESCRIPTION OF THE DRAWINGS

FIG. 3 shows the $^1$H NMR spectrum for the compound of Example 6.

FIG. 4 shows the X-ray powder (XRPD) diffraction diagram for the compound of Example 6.

FIG. 5 shows the DSC diagram for the compound of Example 6.

The Examples hereinbelow illustrate the invention but do not limit it in any way.

EXAMPLE 1: 3-[(3-{[4-(4-MORPHOLINYLMETHYL)-1H-PYRROL-2-YL]METHYLENE}-2-OXO-2,3-DIHYDRO-1H-INDOL-5-YL)METHYL]-1,3-THIAZOLIDINE-2,4-DIONE METHANESULPHONATE, Z ISOMER 1.26 g of 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione are introduced into a 100-mL flask. After adding 20 mL of a solution of acetonitrile/water (90/10), the mixture is heated at 70° C. A solution containing 2 mL of methanesulphonic acid and 50 mL of a mixture of acetonitrile/water (90/10) is prepared. 5 mL of the resulting solution are added to the reaction mixture, which becomes clear. The solution is cooled to 20° C. (0.5° C./min, stirring at 200 rpm). After stirring overnight at ambient temperature, the title product is isolated by filtration, and dried at 40° C. in vacuo (10 mbars).

Melting point: 270-274° C. (melting/decomposition)

The title product is characterised by its powder diffractogram, carried out on 50 mg of the compound of Example 1, placed between 2 Kapton® films or on a support and loaded into a Panalytical Xpert-Pro MPD diffractometer (copper anticathode) in transmission mode with an angular range of 3–55° in terms of 2θ, a step of 0.017° and 35.5 s per step, which makes it possible to identify the following crystal parameters:

unit cell parameters: a=15.0958(5) Å, b=18.4586(6) Å, c=8.8269(2) Å, β=94.074(1°), γ=90° space group: C 1 c 1 (9)

volume of unit cell: $V_{unit\ cell}$=2453.37600 Å$^3$

The title product was also characterised by X-ray diffraction of a single crystal of the compound of Example 1, carried out with a Rigaku XtaLAB apparatus using graphite monochromatic Mo—Kα radiation. The following crystal parameters were observed:

unit cell parameters: a=14.995(4) Å, b=18.302(4) Å, c=8.850(2) Å, β=93.528(7)°, γ=90° space group: C 1 c 1 (9)

volume of unit cell: $V_{unit\ cell}$=2424.0 (9) Å$^3$

The slight differences observed in the parameters obtained using the powder are due to the temperature used to obtain the parameters with the single crystal (–100° C.), which causes a contraction along the axes a and b.

Figure 1:
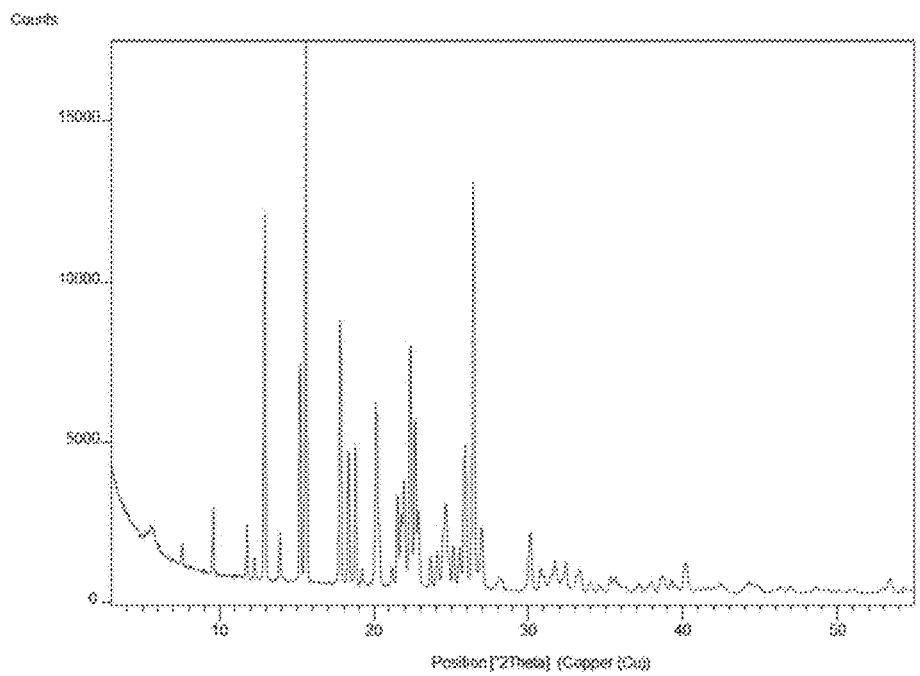
FIG. 1 shows the X-ray powder (XRPD) diffraction diagram for the compound of Example 1.

The title product was also characterised by its X-ray powder diffractogram shown in FIG. 1 and measured using a Panalytical XPert Pro MPD diffractometer (copper anticathode) and expressed in terms of interplanar distance d, Bragg's angle 2 theta (expressed in °±0.2) and relative intensity (expressed as a percentage relative to the most intense line):

| 2-Theta (°) exp. | d (Å) exp. | Intensity (%) |
|---|---|---|
| 12.8678 | 6.87420 | 60.31 |
| 15.1323 | 5.85020 | 38.36 |
| 15.5005 | 5.71203 | 100.00 |
| 17.7050 | 5.00549 | 48.23 |
| 18.2579 | 4.85513 | 23.89 |
| 18.7110 | 4.73856 | 25.22 |
| 20.1109 | 4.41177 | 30.15 |
| 21.4617 | 4.13704 | 16.97 |
| 21.6776 | 4.09632 | 15.77 |
| 21.8970 | 4.05576 | 15.98 |
| 22.2971 | 3.98390 | 41.52 |
| 22.5852 | 3.93372 | 38.20 |
| 24.5702 | 3.62023 | 17.23 |
| 25.8231 | 3.44735 | 24.17 |
| 26.3301 | 3.38211 | 83.15 |

Bragg's angles 2-theta (expressed in °±0.2) characteristic of the X-ray powder diffractogram: 12.86; 15.13; 15.50; 17.70; 18.25; 18.71; 20.11; 21.46; 21.67; 21.89; 22.29; 22.58; 24.57; 25.82; 26.33.

The compound of Example 1 was also characterised by its DSC diagram, for a sample of 5-10 mg loaded into a TA Instruments DSC Q000 apparatus and cooled to 0° C. The sample is then heated to 300° C. at a rate of 10° C./min. The diagram obtained is shown in FIG. 2.

EXAMPLE 2: PURITY AND STABILITY OF 3[(3-{[4-(4-MORPHOLINYLMETHYL)-1H-PYRROL-2-YL]METHYLENE}-2-OXO-2,3-DIHYDRO-1H-INDOL-5-YL)METHYL]-1,3-THIAZOLIDINE-2,4-DIONE METHANESULPHONATE, Z ISOMER, UNDER DENATURING CONDITIONS

Figure 2:
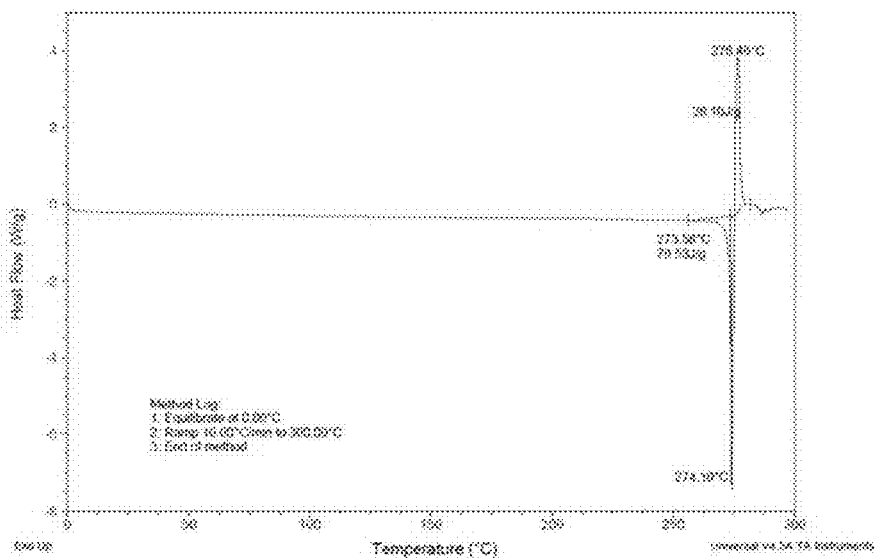
FIG. 2 shows the DSC diagram for the compound of Example 1.

|  | HPLC (% Example 1) | XR | DSC |
| --- | --- | --- | --- |
| t = 0 | 99.8% | FIG. 2 | FIG. 1 |
|  |  | After 6 months |  |
| 25° C./60% relative humidity | 99.8% | Diffractogram unchanged | Thermogram unchanged |
| 25° C./90% relative humidity | 99.8% | Diffractogram unchanged | Thermogram unchanged |
| 30° C./65% relative humidity | 99.8% | Diffractogram unchanged | Thermogram unchanged |
| 40° C./75% relative humidity | 99.8% | Diffractogram unchanged | Thermogram unchanged |
| 50° C. | 99.8% | Diffractogram unchanged | Thermogram unchanged |

EXAMPLE 3: SOLUBILITY OF 3-[(3-{[4-(4-MORPHOLINYLMETHYL)-1H-PYRROL-2-YL]METHYLENE}-2-OXO-2,3-DIHYDRO-1H-INDOL-3-YL)METHYL]-1,3-THIAZOLIDINE-2,4-DIONE METHANESULPHONATE, Z ISOMER

A solution containing 140 mg of the compound obtained in Example 1 in 7 ml of water is stirred for 24 hours at ambient temperature. After filtration using an Acrodisc GJHP 0.45° µm, the solution is analysed by HPLC. The solubility of the compound of Example 1 is 14.7 mg/ml (or 12.1 mg/nil in terms of the base equivalent).

Under the same conditions, the solubility of the hydrochloride of 3-[(3-({[4-{(4-morpholinylmethyl)-1H-pyrrol-2-yl]methylene}-2-oxo-2,3-dihydro-1H-indol-5-yl)methyl]-1,3-thiazolidine-2,4-dione, Z isomer, is 4.3 mg/ml (or 4 mg/ml in terms of the base equivalent).

EXAMPLE 4: DISSOLUTION KINETICS, AT PH 2 (GASTRIC PH), OF 3-[(3-{[4-(4-MORPHOLINYLMETHYL)-1H-PYRROL-2-YL]METHYLENE}-2-OXO-2,3-DIHYDRO-1H-INDOL-5-YL)METHYL]-1,3-THIAZOLIDINE-2,4-DIONE METHANESULPHONATE, Z ISOMER

The constant surface area dissolution kinetics (or intrinsic dissolution kinetics) of the product of Example 1 were determined at ambient temperature at pH 2 (10 mL of 0.01N HCl) using a µDiss dissolution apparatus and pellets of 0.075 cm$^2$, prepared by compression at 90 bars, for 2 minutes at a stirring speed of 100 rpm.

The product of Example 1 dissolves with kinetics of 23 µg·s$^{-1}$·cm$^{-2}$+/−11%. By way of comparison, the dissolution kinetics of the corresponding hydrochloride are 1.6 µg·s$^{-1}$·cm$^{-2}$. The methanesulphonate therefore dissolves about 14 times faster than the corresponding hydrochloride.

EXAMPLE 5: PHARMACEUTICAL COMPOSITIONS 1000 tablets each containing a dose of 5 mg of 3-[3-{[4-(4-morpholinylmethyl)-1H-pyrrol-2-yl]methylene}-2-oxo-2,3-dihydro-1H-indol-5-yl)methyl]-1,3-thiazolidine-2,4-dione

| methanesulphonate, Z isomer (Example 1) | 5 g |
| --- | --- |
| Wheat starch | 20 g |
| Maize starch | 20 g |
| Lactose | 30 g |
| Magnesium stearate | 2 g |
| Silica | 1 g |
| Hydroxypropylcellulose | 2 g |

EXAMPLE 6: 3-[(3-{[4-(4-MORPHOLINYLMETHYL)-1H-PYRROL-2-YL]METHYLENE}-2-OXO-2,3-DIHYDRO-1H-INDOL-5-YL)METHYL]-1,3-THIAZOLIDINE-2,4-DIONE METHANESULPHONATE, E ISOMER

In a pillbox were inserted 113.53 mg of 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione hydrochloride, E isomer, as obtained in Example 1a of U.S. Pat. No. 8,133,889 and K$_2$CO$_3$(3.715 g). This was followed by the addition of distillate water (4 mL) and THF (20 ml). After closing the pillbox, the mixture was stirred 7 minutes at 990 rpm. The resulting upper organic layer was extracted using a syringe and transferred in a pillbox containing the drying agent (Na$_2$SO$_4$). After drying, the organic phase was sucked out with a syringe and transferred into a round bottom flask through another syringe containing a layer of both Na$_2$SO$_4$ and cotton, i.e acting as a "dryer-filter". Under stirring, the yellow organic phase was made acidic using methanesulfonic acid (4.5+9 µL, 0.208 mmol) and the mixture was stirred 2 minutes at 600 rpm. The solvent was evaporated to dryness using a rotary evaporator, thus leading to a yellow oil. The oil was stirred at room temperature in 10 mL of dry acetone for 25 minutes at 990 rpm. The resulting yellow powder was filtered on a Chemrus® disposable filter funnel (20 mL), dried first at 35° C./70 mbar for 1.5 hours and further dried 48 h at 22° C./0.06 mbar. This led to the title compound in a pure yellow crystal.

The NMR resonances of the 1D $^1$H spectrum of compound of Example 6 have been attributed unambiguously by a combination of homonuclear 2D NMR experiments. The spectra obtained are consistent with the chemical structure of compound of the title compound. The $^1$H-NMR spectrum is presented in FIG. 3.

The 2D NOESY spectrum confirms the E configuration of the drug substance.

The proton resonances can be attributed as follows:

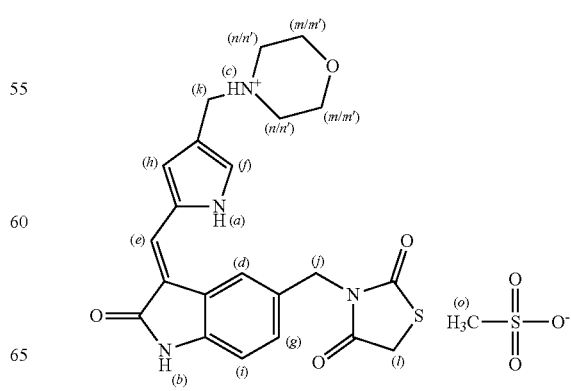

-continued (a) δ = 12.00 ppm (1H; sb)
(b) δ = 10.53 ppm (1H; s)
(c) δ = 9.68 ppm (1H; sb)
(d) δ = 7.99 ppm (1H; s)
(e) δ = 7.47 ppm (1H; s)
(f) δ = 7.37 ppm (1H; sb)
(g) δ = 7.19 ppm (1H; db)   $J_{g'}$ = 7.8 Hz
(h) δ = 7.16 ppm (1H; sb)
(i) δ = 6.84 ppm (1H; d)
(j) δ = 4.65 ppm (2H; s)
(k) δ = 4.30 ppm (2H; d)   $J_{kc}$ = 4.4 Hz
(l) δ = 4.24 ppm (2H; s)
(m) δ = 4.00 ppm (2H; db)   $J_{mm'}$ = 11.8Hz
(m') δ = 3.65 ppm (2H; t)   $J_{m'n'}$ = 11.8Hz
(n) δ = 3.43 ppm (2H; db)   $J_{nn'}$ = 11.8Hz
(n') δ = 3.13 ppm (2H; qb)   $J_{n'c}$ = 11.8Hz
(o) δ = 2.30 ppm (3H; s)

The compound of Example 6 was also characterised by its X-ray powder diffractogram shown in FIG. 4 and measured using a Panalytical XPert Pro MPD diffractometer (copper anticathode) and expressed in terms of interplanar distance d, Bragg's angle 2 theta (expressed in °±00.2) and relative intensity (expressed as a percentage relative to the most intense line):

| Pos. [2Th.] | d-spacing [Å] | Rel. Int. [%] |
| --- | --- | --- |
| 7.5585(2) | 11.68674 | 80.47 |
| 10.4226(7) | 8.4808 | 20.07 |
| 14.8444(7) | 5.963 | 32.02 |
| 15.0672(4) | 5.87532 | 77.27 |
| 15.251(2) | 5.80493 | 19.41 |
| 15.8022(9) | 5.60365 | 22.5 |
| 16.8105(4) | 5.26975 | 94.86 |
| 17.0126(6) | 5.20759 | 46.6 |
| 17.9559(2) | 4.9361 | 100 |
| 19.0697(5) | 4.65023 | 55.2 |
| 20.0024(4) | 4.43546 | 40.58 |
| 20.2924(2) | 4.37271 | 87.03 |
| 21.8806(4) | 4.05878 | 46.56 |
| 23.8752(4) | 3.72401 | 43.45 |
| 24.3164(3) | 3.65744 | 81.22 |
| 24.6414(5) | 3.60993 | 51.38 |
| 26.1348(3) | 3.40694 | 73.04 |
| 26.588(1) | 3.34985 | 36.8 |

Bragg's angles 2-theta (expressed in °±0.2) characteristic of the X-ray powder diffractogram: 7.55; 10.42; 14.84; 15.06; 15.25; 15.80; 16.81; 17.01; 17.95; 19.06; 20.00; 20.29; 21.88; 23.87; 24.31; 24.64; 26.13; 26.59.

The compound of Example 6 was also characterised by its DSC diagram, for a sample of 5-10 mg loaded into a TA Instruments DSC Q1000 apparatus and cooled to 0° C. The sample is then heated to 300° C. at a rate of 10° C./min. The diagram obtained is shown in FIG. 5.

The invention claimed is:

1. E isomer of 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione methanesulphonate of formula (II):

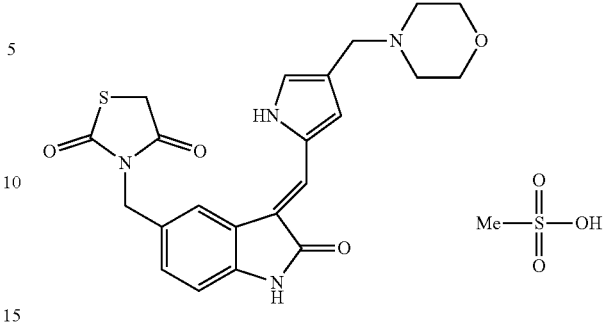

having an X-ray powder diffractogram which exhibits the Bragg's angles 2 theta (expressed in terms of °+0.2) 7.55; 10.42; 14.84; 15.06; 15.25; 15.80; 16.81; 17.01; 17.95; 19.06; 20.00; 20.29; 21.88; 23.87; 24.31; 24.64; 26.13; 26.59.

2. A process for obtaining the compound of formula (II) according to claim 1, wherein 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione is dissolved in a binary system of solvent/water, to which solution from 1 to 2 molar equivalents of methanesulphonic acid are added, stirring until the methanesulphonate precipitates out, which precipitate is filtered off.

3. A process for obtaining the compound of formula (II) according to claim 1, wherein 3-[(3-{[4-(4-morpholinylmethyl)-1H-pyrrol-2-yl]methylene}-2-oxo-2,3-dihydro-1H-indol-5-yl)methyl]-1,3-thiazolidine-2,4-dione hydrochloride is dissolved in a binary system of solvent/water, the pH of which solution is brought to 8 by adding a base, the resulting salt is removed by filtration, the filtrate is then heated and the methanesulphonic acid added, and the medium is stirred and cooled until the methanesulphonate precipitates out, which precipitate is filtered off.

4. A pharmaceutical composition comprising the compound of formula (II) according to claim 1 in combination with one or more pharmaceutically acceptable excipients.

5. A method of treating a condition selected from cancers of the colon, breast, liver, kidneys, brain and esophagus, melanomas, myelomas, ovarian cancers, non-small-cell lung cancers, small-cell lung cancers, prostate and pancreatic cancers, and sarcomas in a subject in need thereof, comprising administration of a compound of formula II according to claim 1 to said subject, optionally in combination with one or more pharmaceutically acceptable excipients.

6. A combination of the compound of formula (II) according to claim 1 with an anti-cancer agent selected from genotoxic agents, mitotic poisons, anti-metabolites, proteasome inhibitors and kinase inhibitors.

7. A method of treating cancer in a subject in need thereof, comprising administration of the combination according to claim 6 to said subject.

8. A method of treating cancer in a subject in need thereof, comprising administration of the compound of formula (II) according to claim 1 to said subject in combination with radiotherapy.

* * * * *